(12) United States Patent
Kang et al.

(10) Patent No.: US 6,764,550 B2
(45) Date of Patent: Jul. 20, 2004

(54) APPARATUS FOR EVALUATING PLASMA POLYMERIZED POLYMER LAYER USING UV SPECTROMETER

(75) Inventors: Sung Hee Kang, Changwon-Shi (KR); Hyun Uk Lee, Changwon-Shi (KR)

(73) Assignee: LG Electronics Inc., Seoul (KR)

( * ) Notice: Subject to any disclaimer, the term of this patent is extended or adjusted under 35 U.S.C. 154(b) by 30 days.

(21) Appl. No.: 09/958,230

(22) PCT Filed: Feb. 6, 2001

(86) PCT No.: PCT/KR01/00172

§ 371 (c)(1),
(2), (4) Date: Nov. 6, 2001

(87) PCT Pub. No.: WO01/86687

PCT Pub. Date: Nov. 15, 2001

(65) Prior Publication Data

US 2003/0047137 A1 Mar. 13, 2003

(30) Foreign Application Priority Data

Feb. 7, 2000 (KR) .......................................... 2000-5606

(51) Int. Cl.⁷ ............................ C23C 16/00; H05H 1/00
(52) U.S. Cl. ................... 118/712; 118/718; 156/345.24
(58) Field of Search ................................ 118/712, 713, 118/718; 156/345.24; 427/8, 434.2

(56) References Cited

U.S. PATENT DOCUMENTS

| 4,488,773 A | 12/1984 | Wagner |
| 4,627,989 A | * 12/1986 | Feuerstein et al. ............ 427/10 |
| 5,225,681 A | 7/1993 | Falk et al. |
| 5,595,781 A | * 1/1997 | Yatsushiro et al. ........... 427/10 |
| 5,759,424 A | * 6/1998 | Imatake et al. ................ 216/60 |
| 5,851,842 A | * 12/1998 | Katsumata et al. ............ 438/9 |

FOREIGN PATENT DOCUMENTS

| EP | 0648858 | 4/1995 | |
| JP | 5-315095 A | * 11/1993 | ............ H05H/1/46 |
| JP | 11-340149 | 12/1999 | |
| JP | 2000309885 A | * 11/2000 | ............ C23C/26/00 |
| KR | 99-088600 | 12/1999 | |

* cited by examiner

*Primary Examiner*—Parviz Hassanzadeh
(74) *Attorney, Agent, or Firm*—Birch, Stewart, Kolasch & Birch, LLP

(57) ABSTRACT

An apparatus for evaluating a performance of a plasma-polymerized polymer layer using a UV spectrometer, including a polymerizing chamber for forming a polymerized polymer layer on a surface of a substrate by plasma discharging, a UV probe mounted contactless to the polymerized polymer layer formed in the polymerizing chamber and transmitting/receiving UV to and from the polymer layer and a UV spectrometer analyzing a signal inputted from the UV probe. With this apparatus, the characteristic of the surface of the substrate having a polymer layer consecutively polymerized by plasma can be evaluated in a contactless way, and the evaluation can be performed without affecting the process parameters such as the degree of vacuum within the chamber.

9 Claims, 2 Drawing Sheets

APPARATUS FOR EVALUATING PLASMA POLYMERIZED POLYMER LAYER USING UV SPECTROMETER

This application is the national phase under 35 U.S.C. §371 of PCT International Application No. PCT/KR01/00172 which has an International filing date of Feb. 6, 2001, which designated the United States of America and was published in English.

FIELD OF THE INVENTION

The present invention relates to an apparatus for evaluating a performance of a plasma polymerized polymer layer using an ultraviolet (UV) spectrometer.

DISCUSSION OF THE BACKGROUND ART

Conventionally, in order to modify a surface of a substrate by synthesizing a polymer, an ion implantation or an ion irradiation method using a high energy (high keV to low MeV) is used, or a polymer is deposited on a surface of a substrate by using an ion beam sputtering deposition which uses an ion source generating particles of a comparatively low energy (O to a few keV), by using a multi-ion beam deposition or by using an ion-assisted deposition.

However, such a method has disadvantages in that it requires a comparatively high energy and a high vacuum state, it is not easy to synthesize a polymer and cost requirements are high.

Thus, there has been proposed a surface modification method using plasma which is capable of forming polymer on the substrate at a low energy and in a low vacuum state.

In this method, a reactive gas including monomers of a material to be synthesized is introduced into a chamber which is placed under vacuum. The gas is then discharged by a direct current or a high frequency by using a power supply unit. Then, plasma of the reactive gas is generated, of which predetermined ions are moved to the substrate or to an electrode, to synthesize a certain polymer thereon.

At this time, various chemical combinations are made depending on the type of reactive gas, a mixed ratio thereof, a direct current/voltage, a high frequency power or a deposition time, etc., so that the surface of the substrate can be modified without affecting the inherent characteristic of the substrate, by depositing polymers having required physical properties such as surface strength, adhesion/adsorption, and hydrophilicity/hydrophobicity on the surface of a substrate.

FIG. 1 shows a schematic view showing the construction of a plasma polymerization apparatus in accordance with the background art.

As shown in FIG. 1, the plasma polymerization is performed in a polymerizing chamber 1 which includes a gas inlet 7, a gas outlet 8, a vacuum pump 9 and an electrode 3 generating a potential difference for the substrate.

For polymerization, the vacuum pump 9 of the polymerizing chamber 1 is actuated to obtain a desired vacuum degree, a reactive gas is introduced through the gas inlet 7, the substrate 2 is conveyed to a winding chamber 5 by passing an unwinding chamber 4 and a roller 6, during which a voltage is applied to the electrode of the polymerizing chamber 1 to generate a potential difference to the substrate 2. Then, as the reactive gas is induced to the surface of the substrate 2, plasma is discharged.

When the plasma is discharged, the molecular bonding of the reactive gases are cut off, and the cut-off bonding and activated positive ions or negative ions are bonded to form a polymer on the surface of the substrate 2 proceeding between the electrodes.

However, up till now, no method has been proposed to effectively evaluate the performance of a polymer layer polymerized on the surface of the substrate 2 which is consecutively modified and wound in a coil form in the winding chamber 5.

SUMMARY OF THE INVENTION

Therefore, an object of the present invention is to provide an apparatus for evaluating a performance of a polymer layer formed on a surface after being consecutively processed without affecting physical and chemical properties of the polymer layer.

Another object of the present invention is to provide an apparatus for effectively evaluating a performance of a polymer layer without affecting a process parameter such as a degree of vacuum of a polymerizing chamber.

In order to achieve the above objects, there is provided an apparatus for evaluating a performance of a plasma-polymerized polymer layer using a UV spectrometer, comprising a polymerizing chamber for forming a polymerized polymer layer on a surface of a substrate by plasma discharging, a UV probe mounted contactless to the polymerized polymer layer formed in the polymerizing chamber and transmitting/receiving UV to and from the polymer layer and a UV spectrometer analyzing a signal inputted from the UV probe.

The UV probe is preferably installed to be sealed from the chamber and installed over a transmission part to transmit the UV.

More preferably, the chamber has a hole in which the transmission part is installed to be sealed to the chamber.

Additionally, an UV probe support means for adjusting the level of the UV probe is additionally installed at an outer wall of the chamber.

Moreover, the transmission part is made of crystal of calcium fluoride.

DETAILED DESCRIPTION OF THE PREFERRED EMBODIMENTS

The present invention will now be described with reference to accompanying drawings.

The present invention discovered that a contactless performance evaluation should be made in order to evaluate a performance of a polymer layer polymerized by using plasma on a surface of a substrate without affecting its physical and chemical properties and that a UV spectrometer is preferable for a contactless evaluation, so as to complete the present invention.

In addition, the present inventors noted that, in evaluating a performance of a polymer layer consecutively polymerized on the surface of a substrate, a process parameter such as a degree of vacuum within the polymerizing chamber in which polymerizing a polymer layer is carried out on the surface of the substrate should be maintained. Therefore, they conducted research on a method for evaluating performance of a polymer layer in a contactless way without affecting the process parameter of the polymerizing chamber, so as to complete the present invention.

Figure 1:
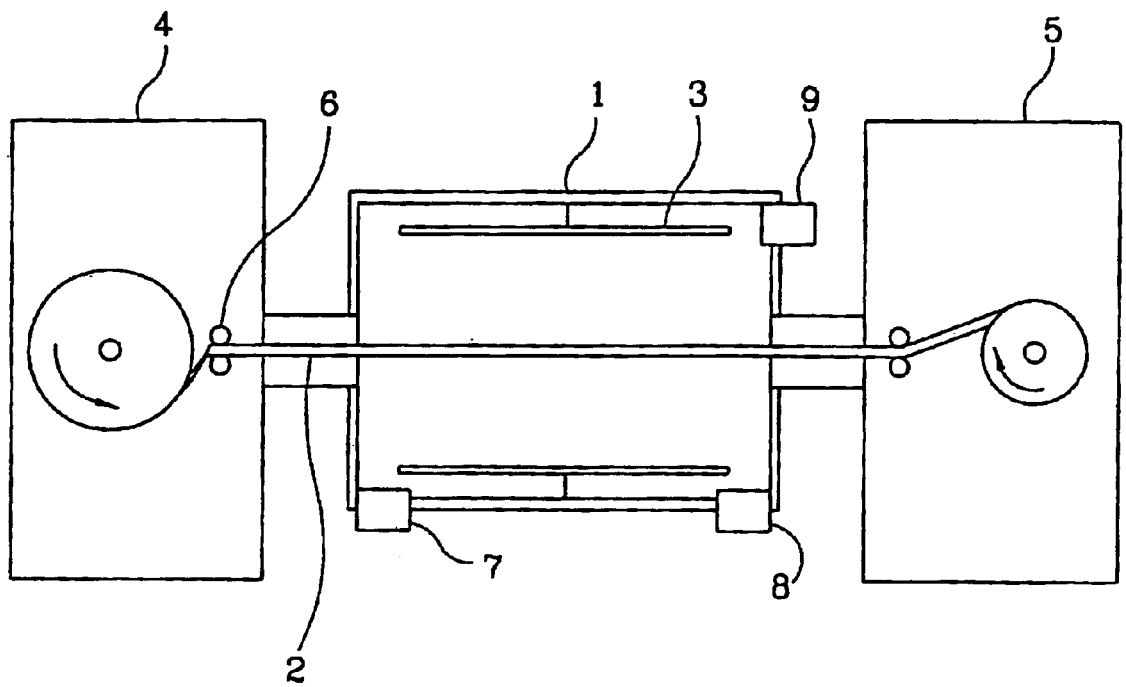
FIG. 1 is a schematic view of a surface modification apparatus using plasma in accordance with the background art.
Figure 2:
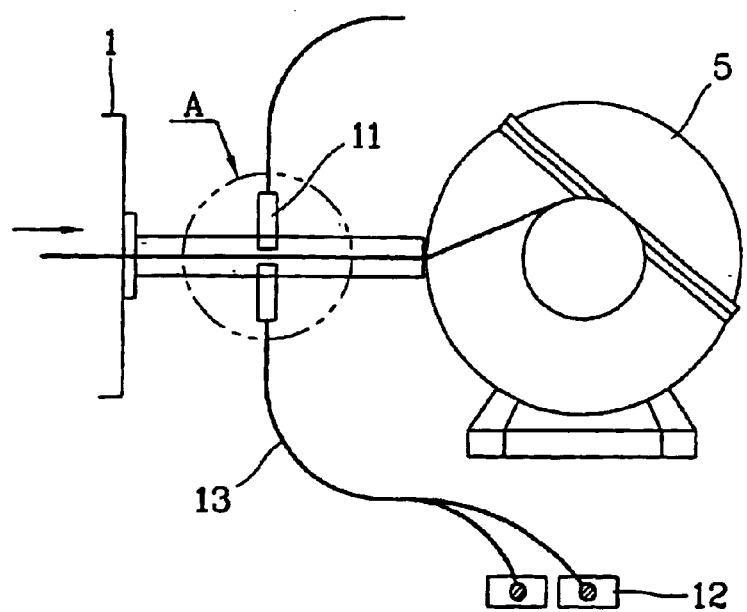
FIG. 2 is a schematic view showing the structure of a UV probe as installed in accordance with one embodiment of the present invention.

FIG. 2 is a schematic view showing the structure of an UV probe 11 as installed in accordance with one embodiment of the present invention.

As shown in FIG. 2, an UV probe 11 is mounted in a passage between a polymerizing chamber 1 and a winding chamber 5. The UV probe is connected through a cable 13 to an UV spectrometer 12.

Because the UV probe 11 is mounted in a manner such that it does not contact the polymer layer formed on the surface of the substrate, and transmits/receives UV thereto and therefrom, it does not affect the physical and chemical properties of the polymer layer.

Though the UV probe 11 is mounted in the passage between the polymerizing chamber 1 and the winding chamber 5, the UV probe may be mounted anywhere as long as it can transmit/receive UV to and from the polymer layer after the polymer layer is completely polymerized by plasma.

That is, the UV probe may be mounted at a proper position within the winding chamber or at end portion of the polymerizing chamber.

In this respect, however, as shown in FIG. 2, in case the UV probe is inserted in the passage, incomplete sealing of the UV probe from the chamber not only affects the process parameters such as the degree of vacuum of the plasma polymerizing chamber 1 but also makes it difficult to operate the UV probe 11 installed in the polymerizing chamber.

Figure 3:
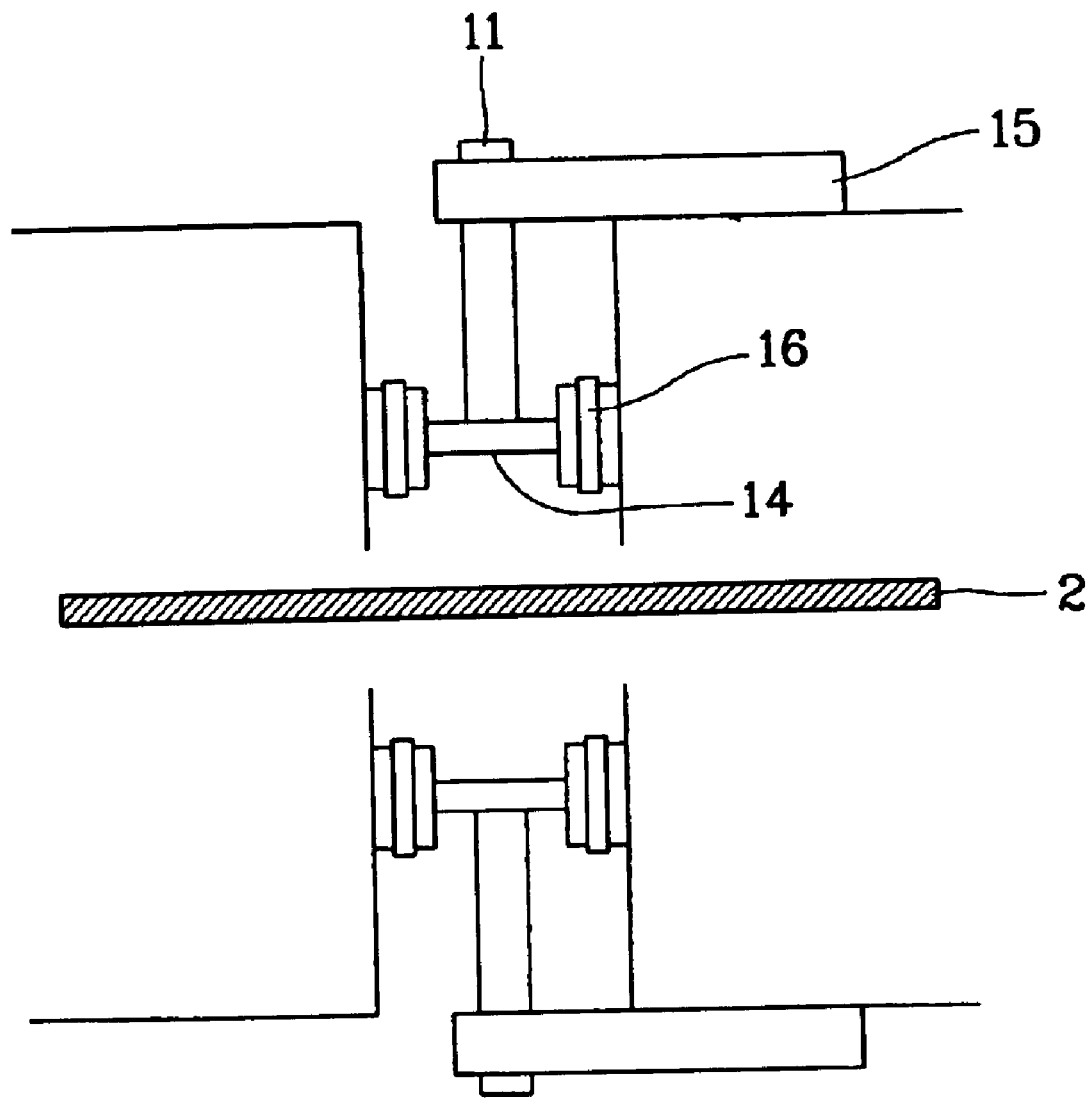
FIG. 3 is a drawing illustrating the structure of a UV probe and a transmission part as installed in accordance with another embodiment of the present invention, to show an enlarged view of portion "A" of FIG. 2.

FIG. 3 is a drawing illustrating a UV probe 11 and a transmission part 14 as installed in accordance with another embodiment of the present invention, which solves the problem of the first embodiment, and an enlarged view of portion "A" of FIG. 2.

That is, the UV probe 11 is installed outside the chamber. For reference, FIG. 3 shows an enlarged view of the portion "A" of FIG. 2.

In order to install the UV probe 11, a hole-like structure is formed at the outer wall of the chamber, in front of which a transmission part 14 is installed.

The transmission part 14 is fixed by a transmission part support 16, and the UV probe 11 is fixed by a UV probe support 15, so that the level of the UV probe 11 can be easily controlled.

Though FIG. 3 shows only that the transmission part can be sealed from the chamber by the transmission part support 14, the transmission part may be also formed at the outer wall of the chamber itself.

In addition, though FIG. 3 shows forming the hole-like structure at the outer wall of the chamber, as mentioned above, it is also possible to form the hole-like structure at the outer wall of the chamber itself. In such case, the UV probe 11 would be installed above the transmission part 14.

In this manner, in the preferred embodiment of the present invention, the performance of the polymerized polymer layer can be evaluated in a contactless way without affecting the process parameters such as the degree of vacuum within the chamber, and the UV probe can be easily manipulated. In addition, by installed the transmission part, a sensor of the UV probe 11 can be protected.

The transmission part is made of a material having a good transmissivity of ultraviolet (UV). Since the wavelength of the UV spectrometer is 200–900 nm, the transmission part is preferably made of crystal ($SiO_2$) or calcium fluoride ($CaF_2$) which are well suited for transmission at wave lengths in that range.

As so far described, according to the present apparatus for evaluating a performance of a plasma polymerized polymer layer using a UV spectrometer, the characteristic of the surface of the substrate having a polymer layer consecutively polymerized by plasma can be evaluated in a contactless way, and the evaluation can be performed without affecting the process parameters such as the degree of vacuum inside the chamber.

What is claimed is:

1. An apparatus for evaluating a performance of a plasma-polymerized polymer layer using a UV spectrometer, comprising:
   a polymerizing chamber for forming a polymerized polymer layer on a surface of a substrate by plasma discharging, said polymerized polymer layer being continuously measured by UV spectroscopy;
   a UV probe mounted polymerized transmitting/receiving UV to and from the polymer layer; and
   a UV spectrometer analyzing a signal inputted from the UV probe.

2. The apparatus according to claim 1, wherein the UV probe is installed to be sealed from the chamber and installed over a transmission part capable to transmit the UV.

3. The apparatus according to claim 2, wherein the chamber has a hole in which the transmission part is installed to be sealed to the chamber.

4. The apparatus according to claim 2, wherein an UV probe support means for adjusting the level of the UV probe is additionally installed at an outer wall of the chamber.

5. The apparatus according to any of claims 2 to 4, wherein the transmission part is made of crystal or calcium fluoride.

6. The polymerization chamber of claim 1, wherein the UV probe is mounted at a position within the winding chamber.

7. The polymerization chamber of claim 1, wherein the UV probe is mounted within the polymerization chamber.

8. The polymerization chamber of claim 7, wherein the UV probe is mounted at an end portion of the polymerization chamber.

9. An apparatus for evaluating a performance of a plasma-polymerized polymer layer using a UV spectrometer, comprising:
   a polymerizing chamber for forming a polymerized polymer layer on a surface of a substrate by plasma discharging, said polymerized polymer layer being continuously measured by UV spectroscopy;
   a UV probe mounted at a portion between the polymerizing chamber and a winding chamber, said UV probe transmitting/receiving UV to and from the polymer layer at said portion; and
   a UV spectrometer analyzing a signal inputted from the UV probe.

* * * * *